United States Patent

Fujishiro

[11] 4,416,763
[45] Nov. 22, 1983

[54] AIR/FUEL RATIO DETECTING DEVICE FOR USE IN EXHAUST GAS OF IC ENGINE

[75] Inventor: Takeshi Fujishiro, Yokosuka, Japan

[73] Assignee: Nissan Motor Co., Ltd., Yokohama, Japan

[21] Appl. No.: 467,879

[22] Filed: Feb. 18, 1983

[30] Foreign Application Priority Data

Feb. 27, 1982 [JP] Japan .................................. 57-31525

[51] Int. Cl.³ .................... G01N 27/58; H01L 7/00
[52] U.S. Cl. .................................. 204/412; 204/408; 204/425; 204/426; 204/429; 338/34
[58] Field of Search ............... 204/412, 425, 426, 429, 204/408; 338/34

[56] References Cited

U.S. PATENT DOCUMENTS

| | | | |
|---|---|---|---|
| 4,007,435 | 2/1977 | Tien | 338/34 |
| 4,107,019 | 8/1978 | Takao et al. | 204/425 |
| 4,207,159 | 6/1980 | Kimura et al. | 204/426 X |
| 4,264,425 | 4/1981 | Kimura et al. | 204/425 X |
| 4,304,652 | 12/1981 | Chiba et al. | 204/425 |
| 4,334,974 | 6/1982 | Muller et al. | 204/425 |
| 4,345,985 | 8/1982 | Tohda et al. | 204/425 X |
| 4,377,801 | 3/1983 | Weber et al. | 338/34 |

Primary Examiner—G. L. Kaplan
Assistant Examiner—Nam X. Nguyen
Attorney, Agent, or Firm—Schwartz, Jeffery, Schwaab, Mack, Blumenthal & Koch

[57] ABSTRACT

A device for use in exhaust gases of internal combustion engines to detect changes in air/fuel ratio. The device has a body of a transition metal oxide, such as $TiO_2$, with a first pair of electrodes attached thereto to measure a change in the resistance of the transition metal oxide in response to a change in the air/fuel ratio. The device includes a combination of a porous layer of an oxygen ion conductive solid electrolyte such as $ZrO_2$ arranged such that the exhaust gas comes into contact with the transition metal oxide body always by diffusion through the solid electrolyte layer and a second pair of electrodes arranged so as to force a DC current to flow in the solid electrolyte from selected one of these electrodes to the other. Migration of oxygen ions in the solid electrolyte layer caused by the flow of the current has the effect of increasing or decreasing the supply of oxygen to the transition metal oxide thereby producing a difference between an oxygen partial pressure at the surface of the transition metal oxide body and the exterior exhaust gas. Therefore, the resistance of the transition metal oxide exhibits a sharp change in response to a change in the air/fuel ratio across a nonstoichiometric ratio which is above or below the stoichiometric ratio depending on the direction of flow of the current.

8 Claims, 18 Drawing Figures

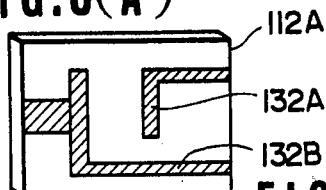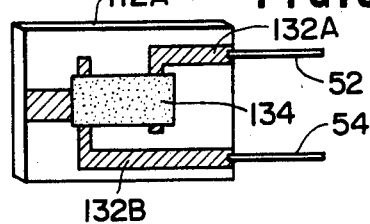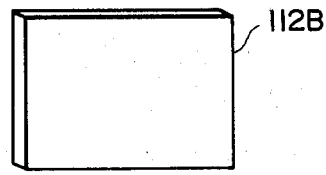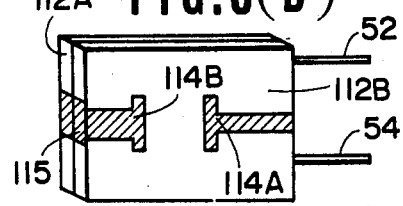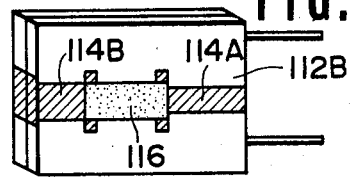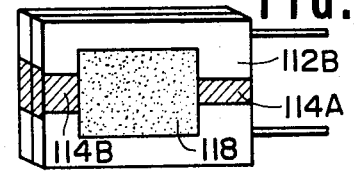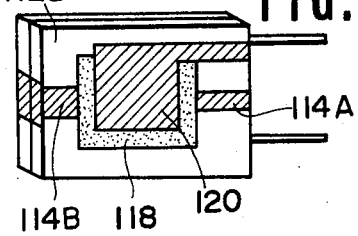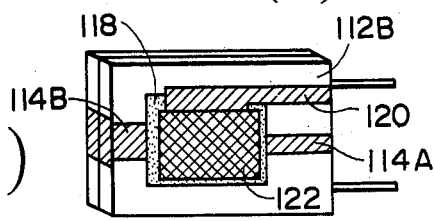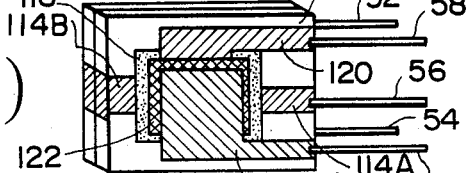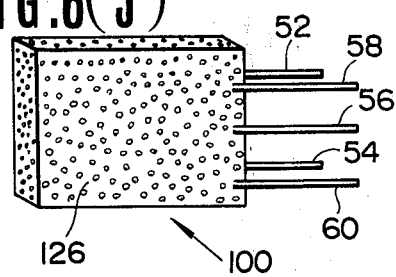

AIR/FUEL RATIO DETECTING DEVICE FOR USE IN EXHAUST GAS OF IC ENGINE

BACKGROUND OF THE INVENTION

This invention relates to an air/fuel ratio detecting device for use in exhaust gases of internal combustion engines operated with either a lean mixture or a rich mixture.

In recent internal combustion engines and particularly in automotive engines, it is prevailing to control the air/fuel mixing ratio precisely to a predetermined optimum ratio by performing feedback control. For example, when a so-called three-way catalyst is used in the exhaust system to achieve reduction of NOx and oxidation of CO and HC simultaneously, the air/fuel ratio is controlled precisely to a stoichiometric ratio because this catalyst exhibits best conversion efficiencies in an exhaust gas produced by combustion of a stoichiometric air-fuel mixture. In the current feedback control systems for this purpose it is usual to provide a feedback signal by sensing changes in the content of oxygen in the exhaust gas since there is a determined relationship between the actual air/fuel ratio in the engine and the oxygen content in the exhaust gas.

It is well known and has been put into industrial practice to produce an oxygen-sensitive device for use in exhaust gases of internal combustion engines by utilizing a semiconductive oxide of a transition metal, such as titania $TiO_2$, since the resistance of such a metal oxide varies in dependence on the partial pressure of oxygen in an environmental gas. Usually titania is used in the form of a sintered body containing a small amount of catalytic material typified by platinum, and in principle an oxygen sensing or air/fuel ratio detecting device can be produced by attaching a pair of electrodes to the sintered titania body to measure the resistance of titania between the two electrodes. In exhaust gases of an internal combustion engine, the resistance of such a titania device remains nearly constantly at a low level while the engine is operated with a fuel-rich air-fuel mixture, but the resistance of this device shifts to a very high level when the engine is operated with a lean mixture. In other words, the resistance or output of the titania device in the exhaust gases exhibits a sharp and great change when the air/fuel ratio in the engine changes across a stoichiometric ratio from a higher value to a lower value or reversely. Accordingly this device is suitable for use in a feedback control system aiming at a stoichiometric air/fuel ratio in an internal combustion engine.

Meanwhile, so-called lean-burn engines in which the air/fuel mixing ratio is considerably higher than a stoichiometric ratio have been developed and put into practice with a view to attaining maximal thermal efficiency. Also, so-called rich-burn engines in which the air/fuel mixing ratio is considerably lower than a stoichiometric ratio have attracted attention because of the possibility of achieving a very high mechanical efficiency and have already been put into industrial practice where recirculation of exhaust gas is employed as a means for decreasing the emission of NOx. Accordingly there is a demand for an air/fuel ratio detecting device which is of use in exhaust gases of internal combustion engines operated with either a fuel-rich mixture or a lean mixture.

SUMMARY OF THE INVENTION

It is an object of the present invention to provide an air/fuel ratio detecting device for use in exhaust gases of internal combustion engines, which device utilizes a transition metal oxide such as titania as the principal material and is responsive to a change in the air/fuel ratio in the engine across a predetermined value that is higher or lower than a stoichiometric air/fuel ratio.

The present invention provides an oxygen-sensitive air/fuel ratio detecting device for use in exhaust gas of an internal combustion engine, which comprises a body of a semiconductive oxide of a transition metal, a first pair of electrodes attached to the transition metal oxide body to measure the resistance of the transition metal oxide existing between these electrodes, and a combination of a microscopically porous layer of an oxygen ion conductive solid electrolyte and a second pair of electrodes attached to the solid electrolyte layer to make a DC current flow in the solid electrolyte layer from a selected one of the second pair of electrodes to the other. The aforementioned combination is arranged such that the exhaust gas comes into contact with the transition metal oxide body always by diffusion through the porous solid electrolyte layer and that the migration of oxygen ions in the solid electrolyte layer caused by the flow of the aforementioned current takes place in substantially the same direction as the diffusion of the exhaust gas toward the transition metal oxide body or in substantially the reverse direction depending on the direction of the flow of the aforementioned current.

Preferred examples of the transition metal oxide are titanium dioxide $TiO_2$, cerium dioxide $CeO_2$ and niobium pentoxide $Nb_2O_5$. It is preferred that the transition metal body contains a small amount of platinum, which serves as oxidation catalyst, in the form of fine particles dispersed in the oxide body.

Examples of the oxygen ion conductive solid electrolyte are $ZrO_2$, $Bi_2O_3$ and $ThO_2$ each containing a small amount of stabilizing oxide such as CaO or $Y_2O_3$.

In the device according to the invention, the transition metal oxide undergoes a change in its electrical resistance in dependence on the content of oxygen in the exhaust gas that comes into contact with the transition metal oxide body through the pores in the solid electrolyte layer. If no current is supplied to the solid electrolyte layer this device functions similarly to conventional oxygen sensors using the same metal oxide, meaning that the resistance of the metal oxide as the output of this device exhibits a sharp change in response to a change in the air/fuel ratio in the engine across a stoichiometric ratio. When a DC current is forced to flow in the solid electrolyte between the second pair of electrodes there occurs migration of oxygen ions in the solid electrolyte layer so that the supply of oxygen to the transition metal oxide is increased or decreased depending on the direction of the migration of oxygen ions or, in other words, depending on the direction of the flow of the current in the solid electrolyte layer. That is, the combination of the solid electrolyte layer and the second pair of electrodes serves the function of an oxygen ion pump. Therefore, an oxygen partial pressure at the surface of the transition metal oxide body becomes above or below the oxygen partial pressure in the exhaust gas flowing around the device. For this reason, the resistance of the transition metal oxide in the device of the invention exhibits a sharp change in response to a change in the air/fuel ratio in the engine across a nonstoichiometric ratio which is higher than or lower than the stoichiometric ratio depending on the direction of flow of the aforementioned current in the device, and the value of the nonstoichiometric air/fuel ratio can be adjusted by controlling the intensity of the current.

Now it will be understood that the device according to the invention is suitable for use in either a lean-burn engine or a rich-burn engine as a device to produce a feedback signal for the control of the air/fuel ratio in the engine.

BRIEF DESCRIPTION OF THE DRAWINGS

FIGS. 6(A) to 6(J) illustrate a process of producing an air/fuel ratio detecting device, which is a slight modification of the device of FIG. 1;

DESCRIPTION OF THE PREFERRED EMBODIMENTS

Figure 1:
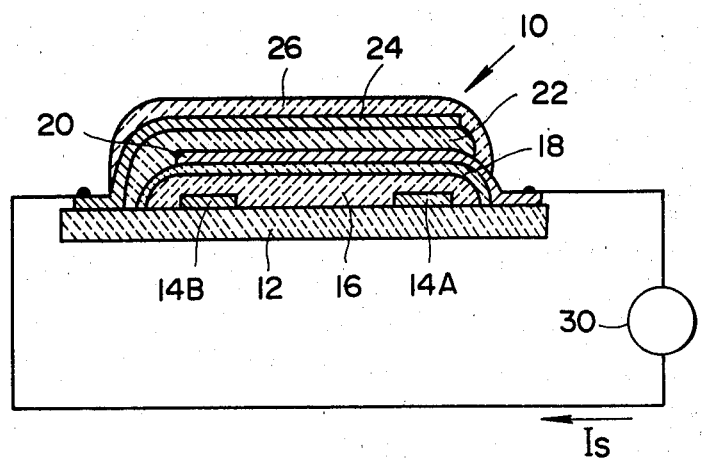
FIG. 1 is a schematic and sectional view of an air/fuel ratio detecting device as an embodiment of the invention.

FIG. 1 shows an air/fuel ratio detecting device 10 according to the invention, which is an oxygen-sensitive element. This device 10 has a substrate 12 made of an electrically insulating and heat-resistant material, such as sintered alumina, as a structurally basic member of the device. The sensitive-part of the device 10 takes the form of a laminate of several relatively thin layers supported on the substrate 12. The laminate can be formed by using a thick-film technique, for example, as will be described hereinafter.

On a major surface of the substrate 12 there are a pair of electrodes 14A and 14B which are suitably spaced from each other. Platinum is a typical material for these electrodes 14A, 14B. Lead wires connected to these electrodes 14A, 14B are omitted from illustration. On the same side of the substrate 12, a layer 16 of titania is formed so as to substantially entirely cover the two electrodes 14A, 14B and to occupy the space between these two electrodes 14A and 14B. Preferably a small amount of platinum in powder form is dispersed in the titania layer 16. The outer surface of the titania layer 16 is entirely covered with an insulating layer 18 which is formed of a ceramic material such as alumina and has a microscopically porous structure permeable to gases. An inner electrode layer 20 is laid on the surface of the insulating layer 18. A layer 22 of an oxygen ion conductive solid electrolyte such as zirconia $ZrO_2$ containing a small amount of stabilizing oxide such as calcia $CaO$ or yttria $Y_2O_3$ is formed so as to cover a substantial area of the inner electrode layer 20, and an outer electrode layer 24 is laid on the outer surface of the solid electrolyte layer 22. Platinum is a typical material for the inner and outer electrode layers 20 and 24. The solid electrolyte layer 22 and the inner and outer electrode layers 20 and 24 are all microscopically porous and permeable to gases. The outer surfaces of the laminate of the above described layers are coated with a porous protective layer 26 formed of a ceramic material.

In the device of FIG. 1 the two innermost electrodes 14A and 14B are used to measure changes in the resistance of the titania 16 existing between these two electrodes 14A and 14B when the device 10 is used in exhaust gases. That is, these two electrodes 14A and 14B correspond to the electrodes in conventional oxygen sensors which utilize the dependence of the resistance of titania on the content of oxygen in an environmental gas.

Figure 2:
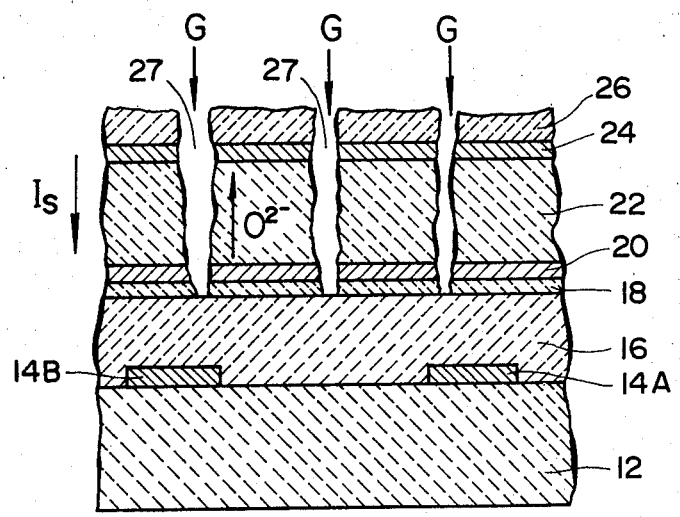
FIG. 2 is a fragmentary and explanatory enlargement of the device of FIG. 1 for explanation of the principle of operation of the device.

The two electrode layers 20 and 24 in contact with the solid electrolyte layer 22 are connectable to a DC power source 30 in order to force a weak DC current $I_s$, of the order of $10^{-5}$ A for example, to flow in the solid electrolyte layer 22 from a selected one of the two electrode layers 20 and 24 to the other during operation of the device 10. In FIGS. 1 and 2 it is assumed that the current $I_s$ flows from the outer electrode layer 24 to the inner electrode layer 20.

Figure 3:
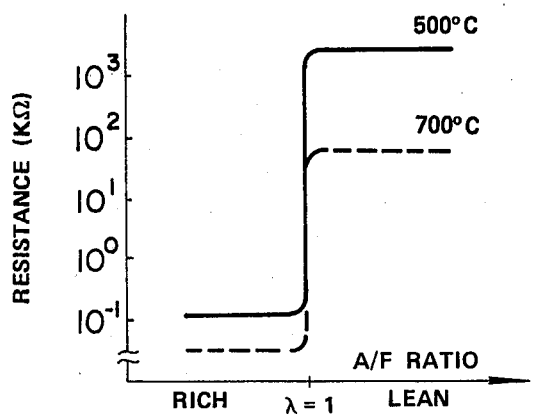
FIGS. 3 to 5 are graphs showing three differently possible and selectable output characteristics of the device of FIG. 1 in exhaust gases of internal combustion engines.

When the device 10 of FIG. 1 is used as a gas sensor without supplying the aforementioned current $I_s$ to the solid electrolyte layer 22, the combination of the solid electrolyte layer 22 and the two electrode layers 20 and 24 serves merely as a gas diffusion layer, so that the gas subject to measurement arrives at the titania layer 16 through the porous insulating layer 18 without undergoing substantial changes in its composition. In that case, therefore, the device 10 of FIG. 1 functions similarly to conventional oxygen sensors using titania. If the gas subject to measurement is exhaust gas of an internal combustion engine, the resistance of the titania 16 between the innermost two electrodes 14A and 14B, i.e. output of the device 10, exhibits a sharp change only when the air/fuel ratio in the engine changes across a stoichiometric ratio where the excess air factor becomes 1.0. That is, the output characteristic of the device 10 of FIG. 1, disregarding the DC power source 30, becomes as shown in FIG. 3. As is known and as can be seen in FIG. 3, the resistance of the titania layer 16 depends on the temperature too.

When the current $I_s$ is supplied to the solid electrolyte layer 22, the same device 10 exhibits a different output characteristic.

Figure 4:
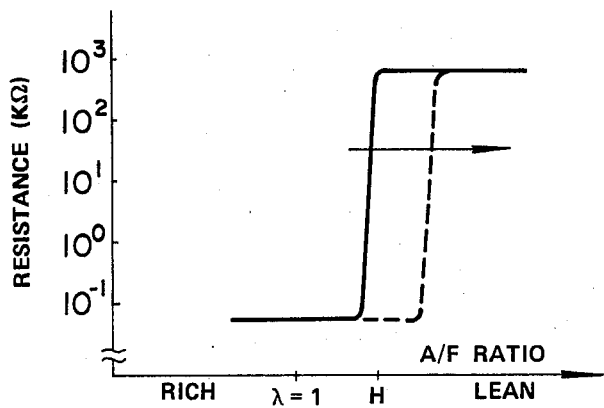

In FIG. 2 reference numeral 27 indicates micropores existing in the porous layers 26, 24, 22, 20 and 18 of the device 10 of FIG. 1. The arrows G prepresent the exhaust gas in which the device 10 is disposed. The pores 27 allow the exhaust gas G to permeate therethrough to arrive at the titania layer 16 whether the current $I_s$ is flowing in the solid electrolyte layer 22 or not. However, the flow of the current $I_s$ in the solid electrolyte 22 from the outer electrode layer 24 to the inner electrode layer 20 causes migration of oxygen ions $O^{2-}$ through the oxygen ion conductive solid electrolyte layer 22 from the inner electrode layer 20 toward the outer electrode layer 24, and therefore an oxygen partial pressure in the vicinity of the inner electrode layer 20 or at the surface of the titania layer 16 remains below the oxygen partial pressure in the exhaust gas flowing around the air/fuel ratio detecting device 10. In other words, it seems to the titania layer 16 in the device 10 in this state that the content of oxygen in the exhaust gas is below the actual oxygen content. Therefore, as shown in FIG. 4, the resistance of the titania layer 16 as the output of the device 10 remains unchanged from a minimally low level even when the air/fuel ratio in the engine changes across a stoichiometric ratio. The resistance of the titania 16 exhibits a sharp change only when the air/fuel ratio changes across a ratio H higher than the stoichiometric ratio, and the value of the air/fuel ratio H depends on the intensity of the current $I_s$ flowing in the solid electrolyte 22 in the direction indicated in FIGS. 1 and 2 and becomes higher as the current $I_s$ is augmented.

Accordingly the device 10 of FIG. 1 with the supply of the current $I_s$ flowing in the direction of the arrow is suitable for application to engines operated with a lean mixture.

Figure 5:
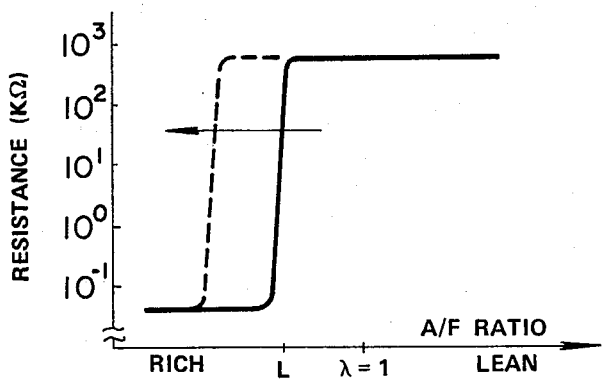

When the current $I_s$ is supplied to the same device 10 so as to flow in the solid electrolyte layer 22 from the inner electrode layer 20 to the outer electrode layer 24, there occurs migration of oxygen ions through the solid electrolyte layer 22 from the outer electrode layer 24 toward the inner electrode layer 20, i.e. in the direction reverse to the arrows in FIG. 2, while gaseous oxygen contained in the exhaust gas diffuse through the micropores 27 toward the titania layer 16. In this case, therefore, an oxygen partial pressure at the surface of the titania layer 16 becomes higher than the oxygen partial pressure in the exhaust gas flowing around the device 10, so that the output characteristics of the device 10 changes inversely to the change in the case of the current $I_s$ flowing from the outer electrode layer 24 to the inner electrode layer 20. As shown in FIG. 5, in this case the resistance of the titania layer 16 as the output of the device 10 remains unchanged from a maximally high level even when the air/fuel ratio in the engine changes across the stoichiometric ratio, but the resistance exhibits a sharp change when the air/fuel ratio changes across a ratio L lower than the stoichiometric ratio. The value of the critical air/fuel ratio L depends on the intensity of the current $I_s$ flowing in the solid electrolyte layer 22 from the inner electrode layer 20 to the outer electrode layer 24 and becomes lower as the current $I_s$ is augmented.

Accordingly the device 10 of FIG. 1 with the supply of a current $I_s$ flowing in the direction reverse to the arrow is suitable for application to engines operated with a rich mixture.

It is preferred to modify the air/fuel ratio detecting device 10 of FIG. 1 by providing a thermistor in series with the resistance of the titania layer 16 for the purpose of compensating the aforementioned dependence of the resistance of this titania layer 16 on the temperature. The provision of a temperature compensating thermistor to the air/fuel ratio detecting device enables to simplify the construction of an electric circuit for treatment of the output of the device.

FIGS. 6(A) to 6(J) illustrate a process of producing a device according to the invention, which is fundamentally similar to the device 10 of FIG. 1 but additionally has a thermistor embedded in the substrate.

Referring to FIGS. 6(A) and 6(C), two sheets 112A and 112B of alumina in a green or unfired state are used to produce the substrate 12 of the device. First, a paste containing platinum powder dispersed in an organic medium is applied onto one (112A) of the two green alumina sheets by screen printing so as to form two paste layers 132A and 132B suitably spaced from each other, followed by drying. When fired subsequently as will be described hereinafter these paste layers 132A, 132B turn into electrode layers. Referring to FIG. 6(B), a pair of lead wires 52 and 54 such as platinum wires are attached to terminal regions of the two platinum paste layers 132A and 132B, respectively, and a paste containing titania powder dispersed in an organic medium is applied onto the green alumina sheet 112A so as to form a paste layer 134 which bridges the gap between the two platinum paste layers 132A and 132B. The titania paste layer 134 is an intermediate of the intended thermistor. Then, the other green alumina sheet 112B is placed on the paste-applied sheet 112A and bonded thereto by application of a suitable pressure.

Referring to FIG. 6(D), the aforementioned platinum paste is applied by screen printing onto the outer surface of the green alumina sheet 112B, which has been bonded to the other alumina sheet 112A, so as to form a pair of paste layers 114A and 114B as intermediate of a pair of electrode layers. The platinum paste is applied to a side face of the laminate of the two alumina sheets 112A, 112B as indicated at 115 for the purpose of providing connection between the newly formed platinum paste layer 114B and the previously formed platinum paste layer 132B. Next, as shown in FIG. 6(E), a paste containing titania powder added with a small amount of platinum powder is applied by screen printing onto the outer surface of the green alumina sheet 112B so as to form a paste layer 116 which bridges the gap between the two platinum paste layers 114A and 114B. Next, as shown in FIG. 6(F), a paste containing alumina powder is applied by screen printing so as to form a paste layer 118 which covers the entire area of the titania paste layer 116.

Referring to FIG. 6(G), the aforementioned platinum paste is applied by screen printing onto the outer surface of the alumina paste layer 118 so as to form a paste layer 120 which has a terminal region extending to an edge of the green alumina sheet 112B. Next, as shown in FIG. 6(H), a paste containing zirconia powder added with a small amount of calcia powder is applied by screen printing so as to form a paste layer 122 on the platinum paste layer 120. Next, as shown in FIG. 6(I), the aforementioned platinum paste is applied by screen printing onto the solid electrolyte paste layer 122 so as to form a platinum paste layer 124 which has a terminal region extending to the aforementioned edge of the green alumina sheet 112B. Then three lead wires 56, 58 and 60 such as platinum wires are attached to the platinum paste layer 114B, to the extended terminal region of the platinum paste layer 120 and to the extended terminal region of the platinum paste layer 124, respectively.

To accomplish simultaneous sintering of the paste layers described with reference to FIGS. 6(A) to 6(I), the laminate shown in FIG. 6(I) is first calcined at about 800° C. and then fired at a higher temperature which may be in the range from about 1200° C. to about 1450° C. Consequently the combination of the two green alumina sheets 112A and 112B turns into a rigid substrate, while the platinum paste layers, titania paste layers and zirconia paste layer turn into rigid but thin and microscopically porous layers, respectively. After that, a porous protective coating layer 126 is formed on the outer surfaces of the sintered laminate, as shown in FIG. 6(J), by plasma-spraying of alumina-magnesia powder for example.

Figure 7:
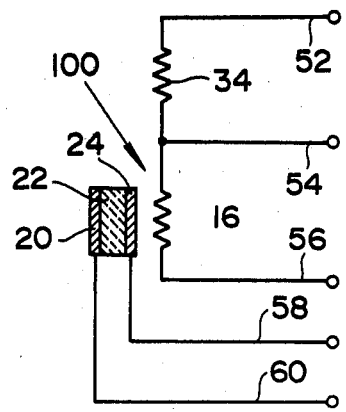
FIG. 7 is a diagram showing the device produced by the process illustrated in FIGS. 6(A) to 6(J)

In principle, the air/fuel ratio detecting device 100 obtained by the process of FIGS. 6(A) to 6(J) is of the construction as illustrated in FIG. 7. In this device 100, titania layer 16 given by the titania paste layer 116 in FIG. 6(E) serves as the sensitive element, and the overlying combination of the oxygen ion conductive solid electrolyte layer 22 and electrode layers 20, 24 serves the function of controlling the partial pressure of oxygen at the titania layer 16 in order to vary the basic output characteristic of the device 100 in the manner as shown either in FIG. 4 or in FIG. 5. The lead wires 58 and 60 are used to supply a DC current to the solid electrolyte layer 22, whereas the lead wires 54 and 56 are used to measure the resistance of the titania layer 16. Indicated at 34 is a thermistor, in the form of the titania layer embedded in the alumina substrate, connected in series with the oxygen-sensitive titania layer 16 to serve the purpose of compensating the temperature dependence of the resistance of the oxygen-sensitive titania layer 16.

It is also preferred to provide a heater element to the device of FIG. 1, because the internal resistances of the titania layer 16 and the solid electrolyte layer 22 and the rate of gas diffusion in these layers significantly depend on the temperature so that the device 10 may not accurately function when the exhaust gas temperature is very low.

Figure 8:
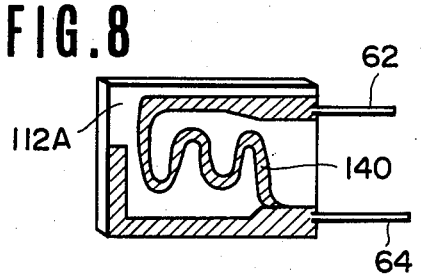
FIG. 8 illustrates a modification of the process of FIGS. 6(A) to 6(J)

Referring to FIG. 8, the addition of a heater to the device 10 of FIG. 1 can be accomplished by modifying the process of FIGS. 6(A) to 6(J) only at the step shown in FIG. 6(B). In this case a paste containing a powder of a suitable electric resistance material, such as platinum, is applied onto the green alumina sheet 112A so as to form a paste layer 140 which is patterned suitably and has two terminal regions extending to an edge of the alumina sheet 112A, and two lead wires 62 and 64 are attached to the extended terminal regions of the platinum paste layer 140. After that the steps of FIGS. 6(C) to 6(J) are performed with no modification. By the firing of the laminate in the state of FIG. 6(I) the platinum paste layer 140 in the substrate is sintered into a platinum layer which serves as an electric heater.

Figure 9:
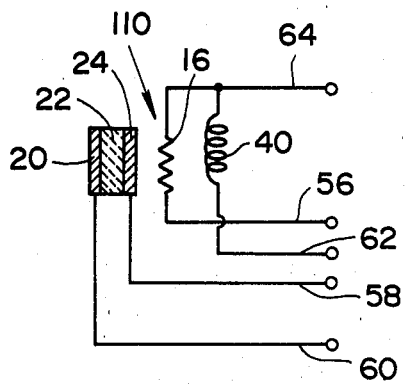
FIG. 9 is a diagram showing an air/fuel ratio detecting device according to the invention, which is produced by modifying the process of FIGS. 6(A) to 6(J) at a step shown in FIG. 8.

In principle, a device 110 obtained by forming the heater layer in this manner is of the construction as illustrated in FIG. 9. Indicated at 40 is the heater layer given by the paste layer 140 in FIG. 8. Where it is desired to heat the device 10 in operation, a suitable voltage is applied to the heater 40 by using the lead wires 62 and 64 from a power circuit (not shown) separate from the power source to force a current to flow in the solid electrolyte layer 22 between the inner and outer electrode layers 20 and 22.

What is claimed is:

1. An oxygen-sensitive air/fuel ratio detecting device for use in exhaust gas of an internal combustion engine, comprising:

a body of a semiconductive oxide of a transition metal;

a first pair of electrodes attached to the transition metal oxide body to measure the resistance of the transition metal oxide existing therebetween; and a combination of a microscopically porous layer of an oxygen ion conductive solid electrolyte and a second pair of electrodes attached to the solid electrolyte layer to make a DC current flow in the solid electrolyte layer from selected one of the second pair of electrodes to the other, said combination being arranged such that the exhaust gas comes into contact with the transition metal oxide body always by diffusion through the porous solid electrolyte layer and that the migration of oxygen ions in the solid electrolyte layer caused by the flow of said current takes place in substantially the same direction as the direction of said diffusion of the exhaust gas toward the transition metal oxide body or in substantially the reverse direction depending on the direction of the flow of said current.

2. A device according to claim 1, wherein the transition metal oxide is selected from the group consisting of titanium dioxide, cerium dioxide and niobium pentoxide.

3. A device according to claim 2, wherein said body of the transition metal oxide contains a catalytic amount of platinum powder dispersed in the transition metal oxide.

4. A device according to claim 1, wherein said solid electrolyte is selected from the group consisting of zirconia, thoria and bismuth trioxide.

5. A device according to claim 1, further comprising a thermistor electrically connected in series with said first pair of electrodes.

6. A device according to claim 1, further comprising an electric heater arranged to heat said body of the transition metal oxide and said layer of the solid electrolyte.

7. A device according to claim 1, wherein said body of the transition metal oxide takes the form of a layer laid on a ceramic substrate, the device further comprising a microscopically porous layer of a heat-resistant and electrically insulating material laid on the outer surface of the transition metal oxide layer, said combination of the solid electrolyte layer and the second pair of electrodes is placed on the outer surface of said layer of the insulating material.

8. A device according to claim 7, wherein said combination takes the form of a laminate consisting of microscopically porous inner electrode layer laid on the outer surface of said layer of the insulating material, said solid electrolyte layer covering the outer surface of said inner electrode layer and a microscopically porous outer electrode layer laid on the outer surface of said solid electrolyte layer.

* * * * *